(12) United States Patent
Myerson et al.

(10) Patent No.: US 7,344,538 B2
(45) Date of Patent: Mar. 18, 2008

(54) MID-FOOT FIXATION PLATE

(75) Inventors: Mark Myerson, Baltimore, MD (US); Priya Prasad, Warsaw, IN (US); Roy Sanders, Tampa, FL (US); Chris Bremer, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 4 days.

(21) Appl. No.: 11/094,994

(22) Filed: Mar. 31, 2005

(65) Prior Publication Data

US 2006/0241592 A1 Oct. 26, 2006

(51) Int. Cl.
*A61B 17/58* (2006.01)

(52) U.S. Cl. .................................................. 606/69

(58) Field of Classification Search ............... 606/61, 606/69–71, 60; 623/17.11, 17.15, 17.16, 623/21.12, 21.15, 21.18, 21.21
See application file for complete search history.

(56) References Cited

U.S. PATENT DOCUMENTS

| | | | |
|---|---|---|---|
| 6,152,927 A * | 11/2000 | Farris et al. ................. 606/69 |
| 6,193,721 B1 * | 2/2001 | Michelson .................... 606/70 |
| 6,344,042 B1 | 2/2002 | Curtis et al. |
| 6,599,290 B2 * | 7/2003 | Bailey et al. ................. 606/69 |
| 6,679,883 B2 * | 1/2004 | Hawkes et al. ............... 606/61 |
| 2002/0077630 A1 * | 6/2002 | Lin ............................... 606/69 |
| 2002/0128654 A1 * | 9/2002 | Steger et al. ................. 606/69 |
| 2004/0102775 A1 | 5/2004 | Huebner et al. |
| 2004/0102778 A1 | 5/2004 | Huebner et al. |
| 2005/0065521 A1 | 3/2005 | Steger et al. |
| 2005/0107795 A1 * | 5/2005 | Morris et al. ................. 606/69 |
| 2006/0025772 A1 * | 2/2006 | Leibel et al. ................. 606/69 |
| 2006/0149249 A1 * | 7/2006 | Mathoulin et al. ........... 606/69 |

* cited by examiner

*Primary Examiner*—Eduardo C. Robert
*Assistant Examiner*—Michael J. Araj
(74) *Attorney, Agent, or Firm*—Maginot, Moore & Beck

(57) ABSTRACT

A fixation device for fixation and/or fusion of the bones and joints of the mid-foot includes a plate having a plurality of screw holes for attachment of the plate around the perimeter of the fusion site. Four screw holes are positioned at the corners of the plate and two screw holes are located at the opposite sides and mid-length of the plate. Four additional screw holes are defined at the interior of the plate to increase the number of points of attachment of the plate to the bones of the mid-foot or to increase the ability to stabilize multiple bone segments in the case of a difficult mid-foot fracture. The plate includes a plurality of cut-outs defined between or interior of the screw holes.

18 Claims, 3 Drawing Sheets

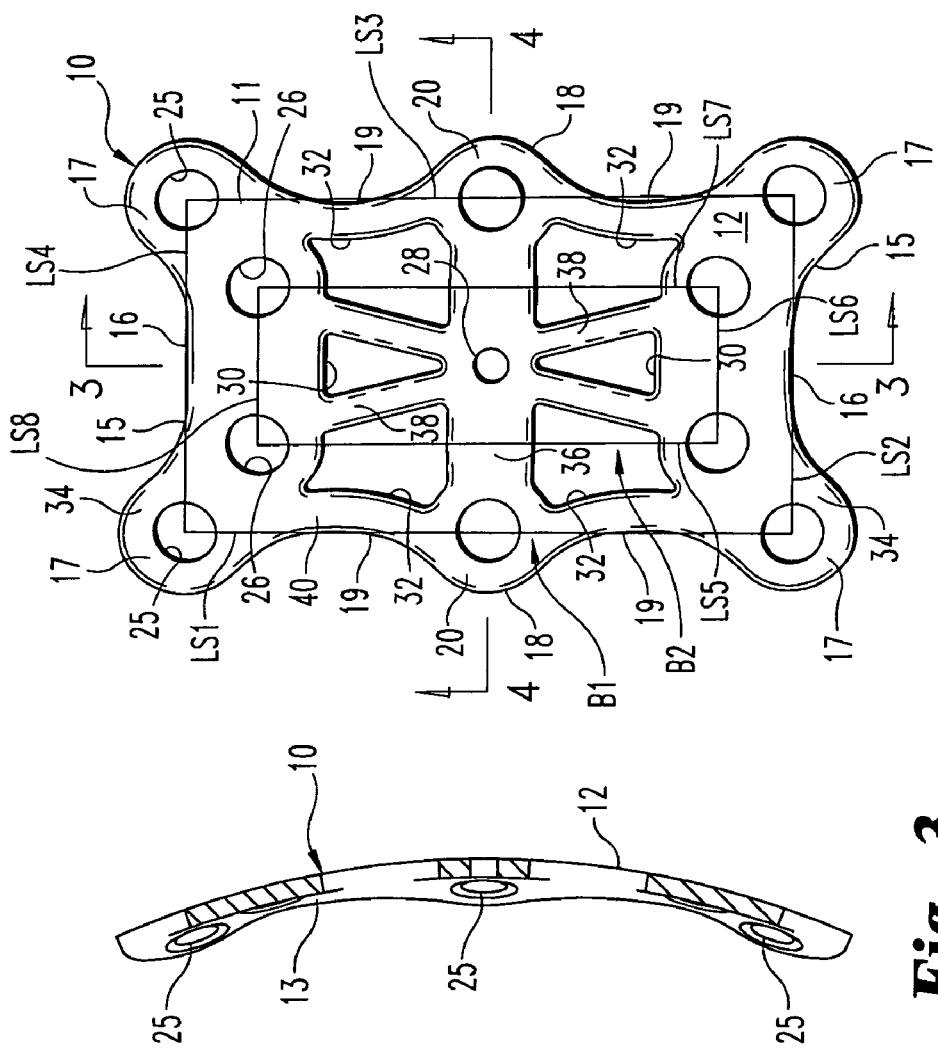

MID-FOOT FIXATION PLATE

BACKGROUND OF THE INVENTION

The present invention relates to plates for fixation of bones and joints. More specifically, the invention pertains to a fixation plate configured for fixation of the mid-foot.

Trauma to the mid-foot often results in severe fractures and/or dislocations. One such trauma is the well-known Lisfranc injury, which was named after the French doctor who first described the injury during the Napoleonic Wars. The injury identified by Dr. Lisfranc occurred when a horseman fell from the horse with his/her foot caught in the stirrup. The resulting trauma was a fracture of multiple bones of the mid-foot with dislocation of the fragments. In modern times, a Lisfranc injury indicates an injury to the normal alignment of the cuneiforms and metatarsal joints with the loss of their normal spatial relationships. Injuries of this type may occur when a heavy item falls on the mid-foot or from stepping into a small hole and then falling with a twisting imparted to the foot. Athletic injuries are common with sports involving foot bindings, such as windsurfing or snow boarding, or sports where the foot is rotated during impact, such as dancing and soccer.

The most common Lisfranc injury occurs at the joint involving the 1st and 2nd metatarsals and the medial cuneiform, primarily because there is no connective tissue holding the first and second metatarsals to each other. If the ligaments between the medial and mid-cuneiforms are disrupted, or between the 1st, 2nd metatarsal and the medial cuneiform, then the bones separate and the normal alignment of the joints is lost. Failure to treat a significant Lisfranc injury may result in joint degeneration and even damage to the adjacent nerves and blood vessels.

Treatment of injuries of this type is usually surgical, especially if a significant separation of the bones exists. One surgical treatment, known as open reduction and internal fixation, usually requires that pins, wires and/or screws be inserted to stabilize the bones and joints and hold them in place until healing is complete. This treatment protocol re-establishes the normal anatomy of the mid-foot while the fractured bones mend. In one typical procedure, a pin or screw is introduced medially into the internal cuneiform and through the base of the second metatarsal bone.

In some cases, fusion of the joint between the first and second metatarsals and the middle and/or internal cuneiforms may be necessary. Arthrodesis may be indicated where arthritis arises in patients with a prior Lisfranc or similar injury, or where an acute fracture/dislocation has occurred anywhere at the mid-foot.

The use of pins, staples or screws is often acceptable for younger patients, especially where the injury is not too severe. However, this form of fixation frequently results in non-union in mid-foot arthrodesis attempts, possibly because the bone fragments and/or joints cannot be sufficiently immobilized by pins, screws or staples alone. Consequently, there is a significant need for a fixation device that provides solid fixation and stabilization of a mid-foot injury. Broad treatment possibilities also requires that the fixation device be capable of multiple points of attachment to the mid-foot bones and bone fragments.

SUMMARY OF THE INVENTION

In view of these needs, the present invention provides a fixation plate that is specifically configured for implantation at the mid-foot. In one embodiment of the invention, a fixation device is in the form of the plate having a plurality of screw holes for attachment of the plate around the perimeter of the fusion site. In one preferred embodiment, four screw holes are positioned in protrusions at the corners of the plate. Two screw holes are positioned in protrusions at the opposite sides and mid-length of the plate.

In a further preferred feature, four additional screw holes are defined at the interior of the plate to increase the number of points of attachment of the plate to the bones of the mid-foot or to increase the ability to stabilize multiple bone segments in the case of a difficult mid-foot fracture. The four additional screws are oriented within the perimeter defined by the six screws formed in the protrusions.

In yet another feature of a preferred embodiment of the invention, a plurality of cut-outs are defined in the plate between or interior of the screw holes. In the most preferred embodiment, two generally triangular cut-outs are positioned along the longitudinal axis of the plate inboard of the interior screw holes, and four larger cut-outs surround the triangular cut-outs, but still fall within the perimeter defined by the screw holes. At least the larger cut-outs are sized for passage of additional bone fasteners, such as screws or pins. The cut-outs may be used to provide additional points of attachment or fixation. In addition, the cut-outs may provide access for a fixation pin or screw to reduce a bone fragment underneath the plate.

The cut-outs are bounded by struts that may be positioned over mid-foot fusion sites or bones to help stabilize the bones or bone segments. The plate is configured so that the screw holes and cut-outs are not oriented over the fusion site(s).

The protrusions and cut-outs help reduce not only the prominence of the plate, but also the material requirements. The plate is also formed at a minimal thickness that still retains the ability to stabilize the fusion site. In a preferred embodiment, the plate has a thickness of less than 1.0 mm. In order to more accurately conform to the local anatomy, the plate is defined at a spherical curvature, which is preferably at a fixed radius.

One benefit of the fixation plate of the present invention is that it is much more versatile than prior devices for achieving fusion of the mid-foot. A further benefit is that the plate offers a plurality of options for bone screw placement to stabilize the mid-foot bones and joints, accomplish firm reduction of bone fractures and ultimately ensure union and/or fusion.

Other benefits and specific objects of the invention will become apparent upon consideration of the following written description taken together with the accompanying figures.

DESCRIPTION OF THE FIGURES

FIG. 2 is a top plan view of the fixation plate shown in FIG. 1.

FIG. 3 is a side cross-sectional view of the plate shown in FIG. 2, taken along line 3-3 as viewed in the direction of the arrows.

FIG. 4 is an end cross-sectional view of the plate shown in FIG. 2, taken along line 4-4 as viewed in the direction of the arrows.

DESCRIPTION OF THE PREFERRED EMBODIMENTS

Figure 1:
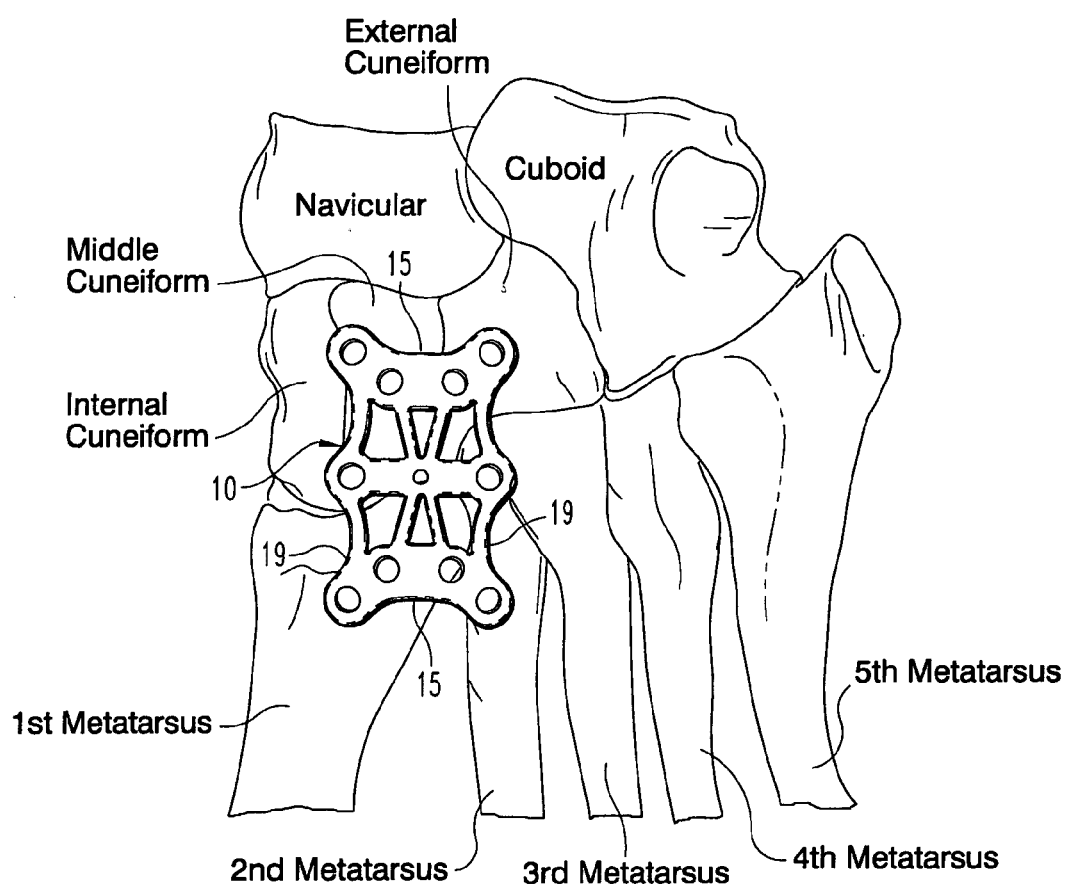
FIG. 1 is an enlarged view of the dorsal aspect of the mid-foot with a fixation plate positioned thereon in accordance with one embodiment of the invention.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The bones of the mid-foot are illustrated from the dorsal aspect in FIG. 1, along with a fixation plate 10 in accordance with a preferred embodiment of the invention. As can be seen in the figure, the plate 10 spans between the base of the first and second metatarsal bones across to the internal (or medial) and middle cuneiforms. In the embodiment illustrated in FIG. 1, the plate 10 is provided that permits attachment to each of the bones of this portion of the mid-foot.

Details of the plate 10 may be gleaned from FIGS. 2-4. The plate 10 is generally configured from a body 11 of generally uniform thickness and material composition. In the preferred embodiment, the body 11 is formed of a biocompatible material, most preferably a metal. In a specific embodiment, the body material is titanium or a titanium alloy, such as Ti-6Al-4V. In order to reduce the prominence of the plate 10 above the bones of the mid-foot, the plate has a nominal thickness between upper surface 12 and bone engaging surface 13 that is minimized while still retaining sufficient strength to ensure solid fixation of the bones and joints of the mid-foot. In a preferred embodiment, the plate has a thickness of less than 1.0 mm, and most preferably about 0.9 mm. This thickness provides sufficient strength while retaining the ability to bend the plate as required to conform to the geometry of the implantation site. In particular, the plate 10 is configured to be positioned anywhere along the mid-foot, not just at the location shown in FIG. 1. Thus, geometry of the middle cuneiform may require a differently contoured plate than a plate positioned across the cuboid bone.

Preferably, however, the plate does not require any on-site contouring since the bone engaging surface 13 is curved in two dimensions to follow the anatomy of the mid-foot, especially across the metatarsal joints. Thus, as shown in the side cross-sectional view of FIG. 3, the surface 13, and hence the plate 10, is curved along the length of the plate. The plate is preferably curved at a uniform radius, such as about 75 mm in a specific embodiment. Similarly, the plate is curved across its width, as reflected in the end cross-sectional view of FIG. 4. This curvature is also at about 75 mm in a specific embodiment. Most preferably, the entire plate is formed at a spherical radius, which may be about 75 mm in the specific embodiment.

The body 11 further includes end edges 15 and side edges 18. In order to reduce material requirements and minimize prominence of the plate 10, the edges define indentations 16 and 19, respectively. As shown in FIG. 1, the end edges 15 define a single indentation 16 that is flanked on opposite sides of the plate by corner protrusions 17. These protrusions 17 merge into the indentations 19 at the side edges 18. An intermediate protrusion 20 is defined on each side edge 18 that is preferably equidistant from each of the corner protrusions 17. In the preferred embodiment, all of the edges 15, 18 are rounded to reduce trauma to the soft tissue surrounding the implant plate.

As shown in FIG. 2, each of the protrusions 17, 20 provides a location for a screw hole 25. Each screw hole is configured to receive a bone engaging fastener configured to attach the plate 10 to the bones of the mid-foot. In the preferred embodiment, the fastener is a bone screw that is appropriately sized for implantation within the base of the metatarsus, any of the cuneiforms or the cuboid bone. The length and diameter of the screw is generally dictated by the location and the size of the bone or bone fragment being fixed. As shown in FIG. 2, the plate 10 includes additional screw holes 26 within the interior of the plate. These screw holes 26 increase the versatility of the plate 10 to provide additional attachment points to a given bone, or to provide a path for fixation of a bone segment, such as in the case of a severe fracture.

The plate 10 of the present invention is specifically configured for implantation and fixation of the mid-foot. Thus, the plate is sized so that the screw holes 25, 26 are optimally positioned for correction and arthrodesis of numerous mid-foot injuries. In a specific embodiment, the plate has a width dimension of about 21.5 mm between the screw holes in the corner protrusions 17 and intermediate protrusions 20. The interior screw holes 26 are preferably at a width dimension of about 10.0 mm. The plate 10 has a length between screw holes 25 at the corner protrusions of about 36.8 mm.

The screw holes 25, 26 are formed at a diameter commensurate with the size of the bone screw used to attach the plate to bone. In the preferred embodiment, the screw holes are configured for 2.7 mm or 3.5 mm screws that are commonly used for fixation of the bones of the foot. In one feature of the invention, the screw holes may include a circumferential chamfer, such as the chamfer 53 for the screw holes 52 of the plate 50 shown in FIG. 5. This configuration of the screw holes allows the plate to accept either size screw at any screw hole location. The present invention further contemplates that the screws may be non-locking or self-locking screws, with the screw holes configured accordingly. In a specific embodiment, locking screws are used and the screw holes 25, 26 define tapered threads (not shown) of conventional design.

A further feature of the invention is best seen in FIG. 2. In particular, the body 11 of the plate defines a plurality of cut-outs, including two cut-outs 32 on each side and two central cut-outs 30, for a total of six cut-outs. The cut-outs 30, 32 reduce the amount of material used to form the plate 10. In addition, the cut-outs create opposite end portions 34 and a center portion 36 spanned by struts 38, 40. The end and center portions 34, 36 carry the screw holes 25, 26. The struts 38, 40 help stabilize the bones or bone segments underneath the struts. The portions 34, 36 and the struts 38, 40 are configured so that screw holes are not located where fusion must occur to stabilize the mid-foot, as reflected in FIG. 1. In the preferred embodiment, the cut-outs 30 are triangular in shape, while the side cut-outs 32 are generally trapezoidal or rectangular in shape. The cut-outs 30, 32 are dimensioned greater than the diameter of the screw holes 25, 26.

In addition to reducing the plate material, the cut-outs 30, 32 provide additional locations for placement of bone screws to augment the fixation or to connect bone segments. In the former case, the bone screws may be positioned at a corner of any of the cut-outs 30, 32. In the latter case, the bone screw is passed through the cut-out and across adjacent bone segments, such as to bridge a fracture. The cut-outs 30 are especially sized to accept a standard bone screw for fixation of mid-foot bone fragments.

In order to facilitate proper placement of the plate 10, a small diameter hole 28 is defined at the center of the plate 10 in the center portion 36. The hole 28 is preferably sized to receive a K-wire or other similar guide wire. In an exemplary procedure for correction of a Lisfranc fracture/dislocation, a K-wire may be inserted into the middle cuneiform to guide the plate 10 across the metatarsus-cuneiform spaces. In one aspect of the invention, the plate 10 provides for screw placement around the perimeter of the mid-foot segments to be fused, in particular with screws placed in the screw holes 25 at the protrusions 17, 20. In some cases, attachment at these locations is sufficient to adequately stabilize the injury for eventual fusion. In other cases, additional screws may be implanted through the screw holes 26 and even through the cut-outs 30, 32. Where bone fragments are present, reduction may be accomplished by passing reduction screws through one or more of the cut-outs 30, 32.

Figure 5:
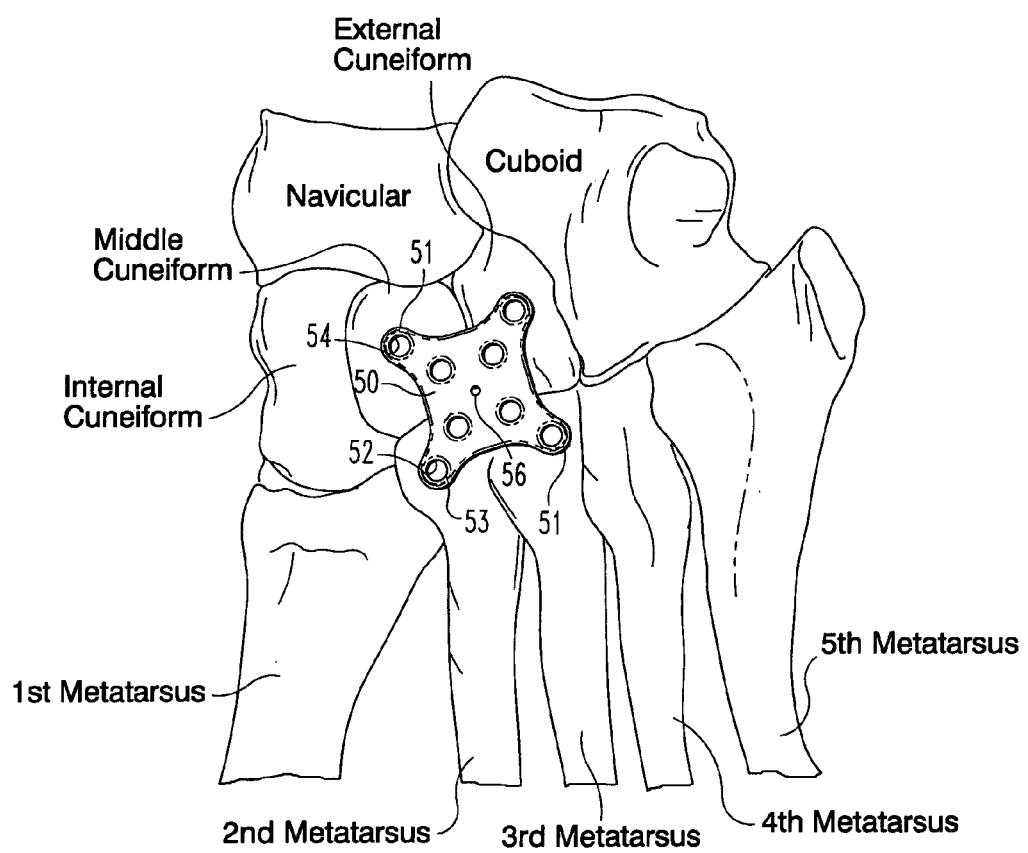
FIG. 5 is an enlarged view of the dorsal aspect of the mid-foot with a fixation plate positioned thereon in accordance with a further embodiment of the invention.

For a smaller mid-foot anatomy or a smaller fusion region, the plate 10 may be modified to form a smaller plate 50, as shown in FIG. 5. This smaller plate retains the spherical curvature and minimal plate thickness described above in connection with the larger plate 10. In addition, the plate 50 includes the corner protrusions 51 which carry the screw holes 52. Screw holes 54 may be provided at the interior of the plate 50 to increase the versatility of the plate. A K-wire hole 56 may also be provided at the center of the plate. The smaller plate 50 is preferably adapted for patients with smaller mid-foot bone and joint structure.

In the preferred embodiment of the invention, a fixation device is in the form of the plate 10 having a plurality of screw holes for attachment of the plate around the perimeter of the fusion site. In the most preferred embodiment, four screw holes are positioned at the corners of the plate with two screw holes at the opposite sides and mid-length of the plate. Preferably, four additional screw holes are defined at the interior of the plate to increase the number of points of attachment of the plate to the bones of the mid-foot or to increase the ability to stabilize multiple bone segments in the case of a difficult mid-foot fracture. In yet another feature of the preferred embodiment, a plurality of cut-outs are defined in the plate between or interior of the screw holes. In the most preferred embodiment, two generally triangular cut-outs are positioned along the longitudinal axis of the plate inboard of the interior screw holes, and four larger cut-outs surround the triangular cut-outs, but still fall within the perimeter defined by the screw holes.

Referring again to FIG. 2, there is shown a first boundary B1 defined by a first quadrilateral created by (i) a first line segment LS1 extending from a first center point of the first circular hole to a second center point of the second circular hole, (ii) a second line segment LS2 extending from the second center point of the second circular hole to a third center point of the third circular hole, (iii) a third line segment LS3 extending from the third center point of the third circular hole to a fourth center point of the fourth circular hole, and (iv) a fourth line segment LS4 extending from the fourth center point of the fourth circular hole to the first center point of the first circular hole.

Continuing to refer to FIG. 2, there is shown a second boundary B2 defined by a second quadrilateral created by (i) a fifth line segment LS5 extending from a fifth center point of the fifth circular hole to a sixth center point of the sixth circular hole, (ii) a sixth line segment LS6 extending from the sixth center point of the sixth circular hole to a seventh center point of the seventh circular hole, (iii) a seventh line segment LS7 extending from the seventh center point of the seventh circular hole to an eighth center point of the eighth circular hole, and (iv) an eighth line segment LS8 extending from the eighth center point of the eighth circular hole to the fifth center point of the fifth circular hole.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A fixation device for fusion of bones or bone segments in the human mid-foot, comprising:

a plate configured to conform to a mid-foot of a patient, said plate defining a plurality of holes, each having a diameter sized for receiving a bone engaging fastener therethrough for attachment of said plate to bone or bone segments of the mid-foot, said plate further defining a plate center point; and said plate further defining a plurality of cut-outs, each dimensioned greater than the diameter of said plurality of holes, wherein said plate further defines (i) a first corner protrusion, (ii) a second corner protrusion, (iii) a third corner protrusion, and (iv) a fourth corner protrusion, wherein said plate further defines (i) a first side edge extending from said first corner protrusion to said second corner protrusion, (ii) a first end edge extending from said second corner protrusion to said third corner protrusion, (iii) a second side edge extending from said third corner protrusion to said fourth corner protrusion, and (iv) a second end edge extending from said fourth corner protrusion to said first corner protrusion, wherein said plurality of holes includes (i) a first circular hole defined in said first corner protrusion, (ii) a second circular hole defined in said second corner protrusion, (iii) a third circular hole defined in said third corner protrusion, and (iv) a fourth circular hole defined in said fourth corner protrusion, wherein a first boundary is defined by a first quadrilateral created by (i) a first line segment extending from a first center point of said first circular hole to a second center point of said second circular hole, (ii) a second line segment extending from said second center point of said second circular hole to a third center point of said third circular hole, (iii) a third line segment extending from said third center point of said third circular hole to a fourth center point of said fourth circular hole, and (iv) a fourth line segment extending from said fourth center point of said fourth circular hole to said first center point of said first circular hole, wherein said plurality of holes further includes (i) a fifth circular hole interposed between said first corner protrusion and said plate center point, (ii) a sixth circular hole interposed between said second corner protrusion and said plate center point, (iii) a seventh circular hole interposed between said third corner protrusion and said plate center point, and (iv) an eighth circular hole interposed between said fourth corner protrusion and said plate center point, wherein each of said fifth circular hole, said sixth circular hole, said seventh circular hole, and said eighth circular hole is positioned within said first boundary, wherein each of said plurality of cut-outs is positioned within said first boundary,
wherein a second boundary is defined by a second quadrilateral created by (i) a fifth line segment extending from a fifth center point of said fifth circular hole to a sixth center point of said sixth circular hole, (ii) a sixth line segment extending from said sixth center point of said sixth circular hole to a seventh center point of said seventh circular hole, (iii) a seventh line segment extending from said seventh center point of said seventh circular hole to an eighth center point of said eighth circular hole, and (iv) an eighth line segment extending from said eighth center point of said eighth circular hole to said fifth center point of said fifth circular hole,
wherein said plate further defines (i) a first side protrusion partially defined by said first side edge and interposed between said first corner protrusion and said second corner protrusion, and (ii) a second side protrusion partially defined by said second side edge and interposed between said third corner protrusion and said fourth corner protrusion,
wherein said plurality of holes further includes (i) a ninth circular hole defined in said first side protrusion, and (ii) a tenth circular hole defined in said second side protrusion, and
wherein each of said ninth circular hole and said tenth circular hole is positioned outside of said second boundary.

2. The fixation device of claim 1, wherein said plate has a substantially uniform thickness less than about 1.0 mm.

3. The fixation device of claim 1, wherein each of said plurality of holes includes a circumferential chamfer.

4. The fixation device of claim 1, wherein said plurality of cut-outs includes a pair of triangular shaped cut-outs arranged along a longitudinal axis of said plate.

5. The fixation device of claim 1, wherein said plurality of cut-outs includes two cut-outs adjacent each side of said plate.

6. The fixation device of claim 5, wherein said two cut-outs adjacent each side are trapezoidal or substantially rectangular in shape.

7. The fixation device of claim 1, wherein said plate further defines a guide wire hole sized to receive a guide wire or K-wire.

8. The fixation device of claim 7, wherein said guide wire hole is aligned with said plate center point.

9. The fixation device of claim 1, wherein said plate includes a bone engaging surface that is curved at a substantially uniform spherical radius.

10. A fixation plate comprising a plate configured to conform to bones of a human foot, wherein:
said plate defines (i) a first corner protrusion, (ii) a second corner protrusion, (iii) a third corner protrusion, and (iv) a fourth corner protrusion,
said plate further defines (i) a first side edge extending from said first corner protrusion to said second corner protrusion, (ii) a first end edge extending from said second corner protrusion to said third corner protrusion, (iii) a second side edge extending from said third corner protrusion to said fourth corner protrusion, and (iv) a second end edge extending from said fourth corner protrusion to said first corner protrusion,
said plate further defines (i) a first circular hole defined in said first corner protrusion, (ii) a second circular hole defined in said second corner protrusion, (iii) a third circular hole defined in said third corner protrusion, and (iv) a fourth circular hole defined in said fourth corner protrusion,
a first boundary is defined by a first quadrilateral created by (i) a first line segment extending from a first center point of said first circular hole to a second center point of said second circular hole, (ii) a second line segment extending from said second center point of said second circular hole to a third center point of said third circular hole, (iii) a third line segment extending from said third center point of said third circular hole to a fourth center point of said fourth circular hole, and (iv) a fourth line segment extending from said fourth center point of said fourth circular hole to said first center point of said first circular hole,
said plate further defines a plate center point,
said plate further defines (i) a fifth circular hole interposed between said first corner protrusion and said plate center point, (ii) a sixth circular hole interposed between said second corner protrusion and said plate center point, (iii) a seventh circular hole interposed between said third corner protrusion and said plate center point, and (iv) an eighth circular hole interposed between said fourth corner protrusion and said plate center point, and
each of said fifth circular hole, said sixth circular hole, said seventh circular hole, and said eighth circular hole is positioned within said first boundary,
wherein a second boundary is defined by a second quadrilateral created by (i) a fifth line segment extending from a fifth center point of said fifth circular hole to a sixth center point of said sixth circular hole, (ii) a sixth line segment extending from said sixth center point of said sixth circular hole to a seventh center point of said seventh circular hole, (iii) a seventh line segment extending from said seventh center point of said seventh circular hole to an eighth center point of said eighth circular hole, and (iv) an eighth line segment extending from said eighth center point of said eighth circular hole to said fifth center point of said fifth circular hole,
wherein said plate further defines (i) a first side protrusion partially defined by said first side edge and interposed between said first corner protrusion and said second corner protrusion, and (ii) a second side protrusion partially defined by said second side edge and interposed between said third corner protrusion and said fourth corner protrusion,
wherein said plurality of holes further includes (i) a ninth circular hole defined in said first side protrusion, and (ii) a tenth circular hole defined in said second side protrusion, and
wherein each of said ninth circular hole and said tenth circular hole is positioned outside of said second boundary.

11. The fixation plate of claim 10, wherein said plate includes:
a first end portion that defines (i) said first protrusion, (ii) said fourth protrusion, and (iii) said second end edge,
a second end portion that defines (i) said second protrusion, (ii) said third protrusion, and (iii) said first end edge, and
a middle portion interposed between said first end portion and said second end portion.

12. The fixation plate of claim 11, wherein:
each of said fifth circular hole and said eighth circular hole is defined in said first end portion of said plate, and each of said sixth circular hole and said seventh circular hole is defined in said second end portion of said plate.

13. The fixation of claim 11, wherein said plate further includes:
a first plurality of struts extending between said first end portion and said middle portion, and
a second plurality of struts extending between said second end portion and said middle portion.

14. The fixation of claim 13, wherein:
a first plurality of cut-outs are defined by (i) said first plurality of struts, (ii) said first end portion, and (iii) said middle portion, and
a second plurality of cut-outs defined by (i) said second plurality of struts, (ii) said second end portion, and (iii) said middle portion.

15. The fixation of claim 14, wherein:
each of said first plurality of cut-outs is positioned within said first boundary, and
each of said second plurality of cut-outs is positioned within said first boundary.

16. A fixation plate comprising a plate configured to conform to bones of a human foot, wherein:
said plate defines (i) a first corner protrusion, (ii) a second corner protrusion, (iii) a third corner protrusion, and (iv) a fourth corner protrusion,
said plate further defines (i) a first side edge extending from said first corner protrusion to said second corner protrusion, (ii) a first end edge extending from said second corner protrusion to said third corner protrusion, (iii) a second side edge extending from said third corner protrusion to said fourth corner protrusion, and (iv) a second end edge extending from said fourth corner protrusion to said first corner protrusion,
said plate further defines (i) a first hole defined in said first corner protrusion, (ii) a second hole defined in said second corner protrusion, (iii) a third hole defined in said third corner protrusion, and (iv) a fourth hole defined in said fourth corner protrusion,
a first boundary is defined by a first quadrilateral created by (i) a first line segment extending from a first center point of said first hole to a second center point of said second hole, (ii) a second line segment extending from said second center point of said second hole to a third center point of said third hole, (iii) a third line segment extending from said third center point of said third hole to a fourth center point of said fourth hole, and (iv) a fourth line segment extending from said fourth center point of said fourth hole to said first center point of said first hole,
said plate further defines a plate center point,
said plate further defines (i) a fifth hole interposed between said first corner protrusion and said plate center point, (ii) a sixth hole interposed between said second corner protrusion and said plate center point, (iii) a seventh hole interposed between said third corner protrusion and said plate center point, and (iv) an eighth hole interposed between said fourth corner protrusion and said plate center point,
each of said fifth hole, said sixth hole, said seventh hole, and said eighth hole is positioned within said first boundary,
said plate includes a first end portion that defines (i) said first protrusion, (ii) said fourth protrusion, and (iii) said second end edge,
said plate further includes a second end portion that defines (i) said second protrusion, (ii) said third protrusion, and (iii) said first end edge,
said plate further includes a middle portion interposed between said first end portion and said second end portion,
said plate further includes (i) a first plurality of struts extending between said first end portion and said middle portion, and (ii) a second plurality of struts extending between said second end portion and said middle portion,
a first plurality of cut-outs are defined by said first plurality of struts, said first end portion, and said middle portion,
a second plurality of cut-outs are defined by said second plurality of struts, said second end portion, and said middle portion, and
each of said first plurality of cut-outs and said second plurality of cut-outs is positioned within said first boundary
wherein a second boundary is defined by a second quadrilateral created by (i) a fifth line segment extending from a fifth center point of said fifth circular hole to a sixth center point of said sixth circular hole, (ii) a sixth line segment extending from said sixth center point of said sixth circular hole to a seventh center point of said seventh circular hole, (iii) a seventh line segment extending from said seventh center point of said seventh circular hole to an eighth center point of said eighth circular hole, and (iv) an eighth line segment extending from said eighth center point of said eighth circular hole to said fifth center point of said fifth circular hole,
wherein said plate further defines (i) a first side protrusion partially defined by said first side edge and interposed between said first corner protrusion and said second corner protrusion, and (ii) a second side protrusion partially defined by said second side edge and interposed between said third corner protrusion and said fourth corner protrusion,
wherein said plurality of holes further includes (i) a ninth circular hole defined in said first side protrusion, and (ii) a tenth circular hole defined in said second side protrusion, and
wherein each of said ninth circular hole and said tenth circular hole is positioned outside of said second boundary.

17. The fixation plate of claim 16, wherein:
each of said fifth hole and said eighth hole is defined in said first end portion of said plate, and
each of said sixth hole and said seventh hole is defined in said second end portion of said plate.

18. The fixation plate of claim 17, wherein:
each of said first side protrusion and said second side protrusion is defined in said middle portion of said plate.

* * * * *